United States Patent [19]
Jurd et al.

[11] 3,936,393
[45] Feb. 3, 1976

[54] ANTIMICROBIAL AGENTS AND USE THEREOF

[75] Inventors: Leonard Jurd, Berkeley; A. Douglas King, Jr., Martinez; William L. Stanley, Richmond, all of Calif.

[73] Assignee: The United States of America as represented by the Secretary of Agriculture, Washington, D.C.

[22] Filed: Apr. 17, 1973

[21] Appl. No.: 351,933

Related U.S. Application Data

[62] Division of Ser. No. 74,485, Sept. 22, 1970, Pat. No. 3,745,222.

[52] U.S. Cl. ............... 252/404; 252/398; 424/346; 426/542; 426/546
[51] Int. Cl.² .................. C09K 15/08; C09K 15/34; A01N 9/00; A23L 3/00
[58] Field of Search ...... 252/404; 424/346; 426/546

[56] References Cited
OTHER PUBLICATIONS

Tetrahedron, 1966, Vol. 21, pp. 2683 to 2696, "The Neoflavanoid Group of Natural Products I".

Chemical Abstracts, Vol. 61, Dec. 1964, article 16477e, "Antibiotic Substances from Higher Plants".

Tetrahedron, 1965, Vol. 21, pp. 2707 to 2715, "The Neoflauanoid Group of Natural Products III".

Hurd et al., Jour. Am. Chem. Soc., Vol. 59, pp. 107–109.

Tetrahedron, Vol. 25, pp. 1407–1416, (1969).

*Primary Examiner*—Benjamin R. Padgett
*Assistant Examiner*—Donald P. Walsh
*Attorney, Agent, or Firm*—M. Howard Silverstein; W. Takacs; Max. D. Hensley

[57] ABSTRACT

Substances which are subject to microbial spoilage are preserved by addition of a cinnamyl phenol, e.g., 2-cinnamylphenol, 4-cinnamyl phenol, 2-methoxy-4-cinnamyl-phenol, 2-cinnamyl-5-methoxy-quinol, etc.

2 Claims, No Drawings

ANTIMICROBIAL AGENTS AND USE THEREOF

A non-exclusive, irrevocable, royalty-free license in the invention herein described, throughout the world for all purposes of the United States Government, with the power to grant sublicenses for such purposes, is hereby granted to the Government of the United States of America.

This is a division of our co-pending application, Ser. No. 74,485, filed Sept. 22, 1970, issued July 10, 1973 as U.S. Pat. No. 3,745,222.

This invention relates to the preservation of substances which are normally subject to microbial spoilage. The objects of the invention include the provision of novel processes and compositions for accomplishing such preservation. Further objects of the invention will be evident from the following disclosure wherein parts and percentages are by weight unless otherwise specified. The abbreviation ppm used herein refers to parts per million. Temperatures are given in degrees Centigrade. The symbol $\phi$ is used herein to designate the phenyl radical.

In accordance with the invention it has been found that certain agents exhibit unexpected antimicrobial activity and are useful for preserving all kinds of materials which are normally subject to microbial spoilage. The agents in question are certain cinnamylphenols, and their antimicrobial activity is unusual and unexpected because it is not shared by closely-related phenol derivatives.

Generically, the agents in accordance with the invention have the structure

I. 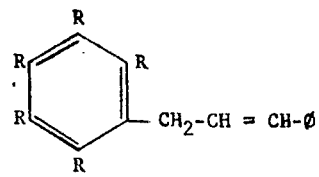

where at least one but not more than three of the R's are hydroxy radicals, and the remainder of the R's are each independently selected from the group consisting of lower alkyl, lower alkoxy, and hydrogen.

The compounds of the invention are especially useful because they are active against many microorganisms in the categories of bacteria, yeasts, and molds. In other words, the compounds are not just active against one or a few organisms; rather, they display broad-spectrum antimicrobial activity.

Examples of particular compounds within the scope of the invention are given below by way of illustration and not limitation:

4-Cinnamyl-phenol (also known as obtusastyrene) 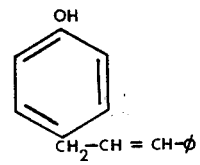

2-Cinnamyl-phenol 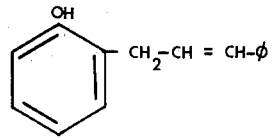

2-Cinnamyl-4-methyl-phenol 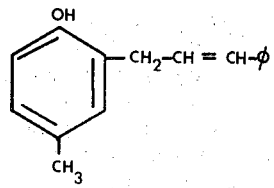

2-Cinnamyl-4-methoxy-phenol 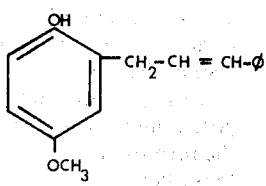

2-Methyl-4-cinnamyl-
phenol

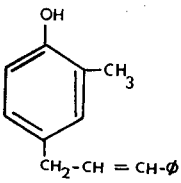

2-Methoxy-4-cinnamyl-
phenol

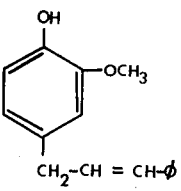

4-Cinnamyl-resorcinol

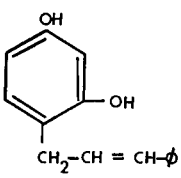

2-Cinnamyl-5-methoxy-
quinol

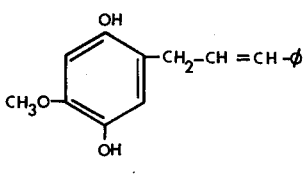

4-Cinnamyl-pyrogallol

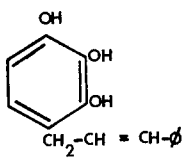

The compounds of the invention display activities which are equal or even superior to those of widely-used antimicrobial agents. This is illustrated by the following: In general, the compounds of the invention are superior to such known agents as phenol, resorcinol, o-phenyl-phenol, and the alkali metal sorbates and benzoates. For instance, compounds of the invention, at concentrations of 12 to 25 ppm, were found to inhibit the growth of four bacteria (*Bacillus cereus, Sarcina lutea, Staphylococcus aureus,* and *Streptococcus lactis*) whereas to achieve the same effect it required 100 to 200 ppm of o-phenyl-phenol, more than 800 ppm of potassium sorbate, and more than 1000 ppm of sodium benzoate.

Alkyl 4-hydroxybenzoates are well known to exhibit potent microbial activity. In general, the compounds of the invention display a superior activity as compared to these benzoates wherein the alkyl group contains less than seven carbon atoms. For instance, whereas the compounds of the invention at a concentration of 12 to 25 ppm will inhibit the growth of the four bacteria noted above, it requires concentrations of 100 to 400 ppm for the same result to be achieved with the $C_1$-$C_5$ alkyl 4-hydroxybenzoates. Moreover, it may be noted that the compounds of the invention have an advantage in that their water-solubility is higher than that of the higher alkyl (e.g., heptyl) 4-hydroxybenzoates, and that the compounds of the invention do not exhibit the strong and unpleasant odor which characterizes the said benzoates. Also, with respect to some microorganisms, the compounds of the invention inhibit growth when applied at levels less than required with the higher alkyl 4-hydroxybenzoates. This is the case, for example, with bacteria such as *Acaligenes faecelis* and *E. coli*, yeasts such as *Pichia chodati, Hansenula anomala,* and *Saccharomyces cerevisiae*, and molds including *Aspergillus flavus*, A. niger, *Penicillium chrysogenum, Rhizopus senti, Botrytis cinerea, Byssochlamys*

*fulva*, and *Alternaria sp.*

Of the various compounds included within the scope of the invention, the cinnamyl-substituted monophenols display particularly high antibiotic activity against a large variety of different microorganisms, and therefore are preferred with respect to the cinnamyl derivatives of di- or tri-phenols. Coming into special consideration is 4-cinnamyl-phenol because it displays antibiotic activity over a wide range of pH. The cinnamyl derivative of monophenols are also preferred because they are essentially colorless, whereas those derived from di- or tri-phenols exhibit various shades varying from red to brown.

As evident from the explanation immediately following Formula I above, the invention includes compounds wherein there may be nuclear lower alkyl or lower alkoxy substituents in addition to the hydroxy groups. In general, the compounds are preferred wherein such additional substituents are absent or, if present, are in small number, e.g., a total of one to two lower alkyl and/or lower alkoxy substituents. Taking the foregoing facts into consideration, we prefer to employ the compounds of the sub-generic category represented by the formula

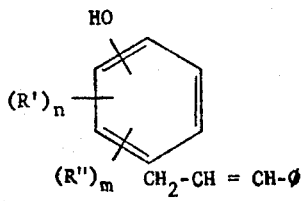

wherein
R' is lower alkyl,
R'' is lower alkoxy,
$n$ is an integer from 0 to 2,
$m$ is an integer from 0 to 2, and
the sum of $n$ and $m$ is not more than 2.

The invention encompasses not only the use of any of the above-described agents individually, but also mixtures thereof.

In preserving substances in accordance with the invention, any of the aforesaid agents or mixtures thereof are incorporated with the substance, using an amount of the agent to inhibit microbial growth. Additional conventional treatments such as dehydration, canning, refrigeration, or freezing may be applied to the substance containing the added agent. The incorporation of the agent with the substance may involve a mixing of the substance and the agent—this is especially suitable where the substance is in liquid or particulate form. Where the substance is in the form of pieces of large dimensions the agent may be incorporated therewith by coating it on the surface of the pieces. For such purpose the agent is preferably dispersed in a carrier—a liquid such as water, alcohol, water-alcohol blends, oils, or a finely-divided solid such as salt, starch, talc, or the like.

The invention is of wide versatility and can be applied for the preservation of all kinds of substances which are normally subject to microbial spoilage. Typical examples of such substances are listed below by way of example. Foodstuffs such as fruits, vegetables, juices, milk, eggs, meat, fish, grains, cereal products, cheese, etc. Animal glues and mucilages; dextrins; starch pastes and solutions; cosmetic, medicinal, and dental preparations; vitamin preparations; pastes, solutions, or other preparations of natural gums such as tragacanth, Arabic, acacia, karaya, locust bean, agaragar, pectin, elgin, etc.; fermentation broths, mashes, and residues from fermentation processes; whey; wines and vinegars; animal feeds and ingredients of animal feeds such as fish meals, blood meals, feather meal, meat scraps, bone meal, tankage, grains, and oil-seed meals; proteins and protein hydrolysates; textile printing pastes; paints containing proteins or other spoilable dispersing agents; solutions of bark extracts or other tanning agents; molasses; by-products or wastes that contain potentially valuable carbohydrate, proteinous or fat ingredients such as stick liquor, corn steep liquor, fruit cannery wastes, citrus peels, cull fruit and vegetables, tops of root vegetables, distillers' slops, pulp liquors, wash water from textile de-sizing operations, waste liquors from wool scouring plants, dairy and slaughter house wastes and liquors, etc.

The compounds of the invention may be synthesized by known procedures—for example, those disclosed by Hurd et al, Jour. Am. Chem. Soc., Vol. 59, pp. 107–109; Barnes et al, Tetrahedron, Vol. 21, pp. 2707–2715; Jurd, Experientia, Vol. 24, pp. 858–860; Jurd, Tetrahedron, Vol. 25, pp. 1407–1416; and Jurd, Tetrahedron Letters No. 33, pp. 2863–2866. Typically, these syntheses involve condensing a selected phenol (phenol itself, a cresol, resorcinol, guaiacol, hydroquinone monomethyl ether, etc.) with cinnamyl bromide or cinnamyl alcohol.

The invention is further demonstrated by the following illustrative examples. For comparative purposes, various compounds, including some of known antimicrobial activity, are included in the reported experiments.

EXAMPLE 1

A series of compounds were assayed for effectiveness against bacteria, molds, and yeasts, using the following test procedure.

All compounds were tested at a concentration of 500 ppm. (w/v). Plates were prepared by adding a measured amount of the candidate compound (in an appropriate solvent, i.e., acetone, ethanol, or water) to 10 ml. of sterilized medium, mixing thoroughly, pouring into 60 × 15 mm. Petri dishes, and allowing the gel to set. The plates were then inoculated with the test organisms. In the case of bacteria and yeasts the inoculation was done by Lederberg's replica plating technique, applying nine bacteria or seven yeasts on each plate. In the case of molds, drops of homogenized culture were placed on the surface of the plates, applying three to four molds per plate.

The media used were: plate count agar (Difco) for bacteria; potato dextrose agar (Difco) for yeasts and molds.

Control plates were also prepared containing the media plus the same solvent used for the candidate agents and inoculated with the same organisms.

The plates were incubated at 28° C. for one to five days and evaluated by comparison with the controls.

The results are expressed on the basis:
+ for effective to inhibit growth
± for not completely effective; faint growth occurs
− for ineffective; growth occurs
The results are summarized in the following tables.

Table I

Activity of Various Compounds (at conc. of 500 ppm) Against Bacteria

| | 4-Cinna-myl-phenol | 4-Cinna-myl-resor-cinol | 4-Cinna-myl-pyro-gallol | 2-Cinna-myl-5-me-thoxy-qui-nol | 2-Cinna-myl-5-me-thoxy-qui-none | Cinnamyl-eugenol | Phenol | Resor-cinol | Pyro-gallol | Methoxy-quinol |
|---|---|---|---|---|---|---|---|---|---|---|
| Bacillus cereus | + | + | + | + | − | + | − | − | + | + |
| Sarcina lutea | + | + | + | + | − | − | − | − | + | − |
| Staphylococcus aureus | + | + | + | + | − | − | − | − | + | − |
| Streptococcus lactis | + | + | + | + | − | + | − | − | + | + |
| Acaligenes faecalis | + | + | + | + | − | − | − | − | + | + |
| Escherichia coli | + | + | ± | − | − | − | − | − | + | + |
| Pseudomonas aeruginosa | − | − | + | − | − | − | − | − | + | + |
| Salmonella typhimurium | − | + | ± | − | − | − | − | − | + | − |
| Serratia marcescens | − | − | ± | − | − | − | − | − | ± | − |

Table II

Activity of Various Compounds (at conc. of 500 ppm) Against Yeasts

| | 4-Cinna-myl-phenol | 4-Cinna-myl-resor-cinol | 4-Cinna-myl-pyro-gallol | 2-Cinna-myl-5-me-thoxy-qui-nol | 2-Cinna-myl-5-me-thoxy-qui-none | Cinnamyl-eugenol | Phenol | Resor-cinol | Pyro-gallol | Methoxy-quinol |
|---|---|---|---|---|---|---|---|---|---|---|
| Zygosaccharomyces japonicus | + | + | + | + | + | − | − | − | + | − |
| Candida tropicalis | + | + | + | + | + | + | − | − | + | + |
| Pichia chodati | + | + | + | − | − | − | − | − | − | − |
| Hansenula anomala | + | + | + | − | − | − | − | − | − | − |
| Saccharomyces cerevisiae | | | | | | | − | − | + | |
| Saccharomyces mellis | + | + | + | + | + | − | | | | + |
| Torula utilis | + | + | + | − | − | − | − | − | + | |
| Hansenula melliqui | + | + | + | + | − | − | | | | |
| Candida chalmersi | + | + | + | + | + | + | | | | + |
| Saccharomyces rosei | + | + | + | + | − | − | | | | − |
| Zygosaccharomyces barkeri | + | + | + | + | − | − | | | | − |

Table III

Activity of Various Compounds (at conc. of 500 ppm) Against Molds

| | 4-Cinna-myl-phenol | 4-Cinna-myl-resor-cinol | 4-Cinna-myl-pyro-gallol | 2-Cinna-myl-5-me-thoxy-qui-nol | 2-Cinna-myl-5-me-thoxy-qui-none | Cinnamyl-eugenol | Phenol | Resor-cinol | Pyro-gal-lol | Methoxy-quinol |
|---|---|---|---|---|---|---|---|---|---|---|
| Aspergillus flavus | + | + | + | − | − | − | ± | − | − | − |
| Aspergillus niger | + | + | + | − | − | − | ± | − | − | − |
| Penicillium chrysogenum | + | + | + | − | − | − | − | − | ± | − |
| Rhizopus senti | + | + | + | − | − | − | − | − | − | − |
| Botrytis cinerea | + | + | + | − | − | − | + | − | + | − |
| Byssochlamys fulva | + | + | + | + | − | − | ± | + | + | − |
| Alternaria sp. | + | + | + | − | − | − | ± | + | + | |

EXAMPLE 2

A series of compounds were assayed for effectiveness against bacteria, molds, and yeasts as set forth in Example 1, except that in this case the assays were conducted with varying amounts of each compound to determine the minimum concentration thereof required to inhibit growth.

The results are set forth in the following tables.

Table IV

Minimal Inhibitory Concentrations (in ppm.) of Various Compounds Against Bacteria

| | 4-Cinnamyl-phenol | 2-Cinnamyl-phenol | 2-Cinnamyl-4-methoxy-phenol | 2-Methyl-4-cinnamyl-phenol | 2-Cinnamyl-4-methyl-phenol | Ortho-phenyl-phenol | Potassium sorbate | Sodium benzoate |
|---|---|---|---|---|---|---|---|---|
| Bacillus cereus | 25 | 12 | 25 | 12 | 12 | 100–200 | >800 | >1000 |
| Sarcina lutea | 25 | 25 | 25 | 12 | 12 | 200 | do. | do. |
| Staphylococcus aureus | 25 | 25 | 25 | 12 | 12 | 200 | do. | do. |
| Streptococcus lactis | 25 | 12 | 25 | 12 | 12 | 100–200 | do. | do. |
| Acaligenes faecalis | 50–100 | >200 | >200 | >200 | >200 | 100–200 | do. | do. |
| Escherichia coli | 50–100 | >200 | >200 | >200 | >200 | 100–200 | do. | do. |

Table V

Minimal Inhibitory Concentrations (in ppm.) of Various Compounds Against Yeasts

| | 4-Cinnamyl-phenol | 2-Cinnamyl-phenol | 2-Cinnamyl-4-methoxy-phenol | 2-Methyl-4-cinnamyl-phenol | 2-Cinnamyl-4-methyl-phenol | o-phenyl-phenol | Potassium sorbate | Sodium benzoate |
|---|---|---|---|---|---|---|---|---|
| Zygosaccharomyces japonicus | 12 | 12 | 25 | 12 | 12 | 100–200 | 800 | >1000 |
| Candida tropicalis | 12 | 12 | 50 | 25 | 25 | 100 | 200–400 | 250–500 |
| Pichia chodati | 25 | 50 | >200 | 200 | >200 | 100 | 800 | >1000 |
| Hansenula anomala | 50 | 50 | 100 | 100 | 50 | 100–200 | 800 | do. |
| Saccharomyces cerevisiae | 25 | 25 | 50 | 25 | 25 | 100–200 | 800 | do. |
| Torula utilis | 50 | 50 | >200 | 100 | >200 | 100–200 | 800 | do. |

Table VI

Minimal Inhibitory Concentrations (in ppm.) of Various Compounds Against Molds

| | 4-Cinnamyl-phenol | 2-Cinnamyl-phenol | 2-Cinnamyl-4-methoxy-phenol | 2-Methyl-4-cinnamyl-phenol | 2-Cinnamyl-4-methyl-phenol | o-phenyl-phenol | Potassium sorbate | Sodium benzoate |
|---|---|---|---|---|---|---|---|---|
| Aspergillus flavus | 100 | 100 | >200 | >200 | >200 | 100 | >800 | >1000 |
| Aspergillus niger | 50 | 100 | >200 | >200 | >200 | 100 | do. | do. |
| Penicillium chrysogenum | 50 | 25–50 | 200 | 50 | 100 | 50 | do. | do. |
| Rhizopus senti | 6 | 50 | >200 | 50 | 100 | 100 | 200 | 500 |
| Botrytis cinerea | 25–50 | 12–25 | 200 | 50 | 25 | 12–25 | 200 | 500 |
| Byssochlamys fulva | 25 | 25 | 50 | 25 | 25 | 50 | >800 | >1000 |
| Alternaria sp. | 25 | 25 | 100 | 50 | 100 | 50 | 400 | 500 |

Table VII

Minimal Inhibitory Concentrations (in ppm.) of 4-Cinnamyl-phenol and Several Alkyl 4-Hydroxybenzoates Against Bacteria, Yeasts, and Molds

| | 4-Cinnamyl-phenol | Heptyl-4-hydroxybenzoate | Amyl 4-hydroxybenzoate | n-Butyl 4-hydroxybenzoate | n-Propyl 4-hydroxybenzoate | Ethyl 4-hydroxybenzoate | Methyl 4-hydroxybenzoate |
|---|---|---|---|---|---|---|---|
| Bacillus cereus | 25 | 12 | 100 | 200 | 400 | >200 | >200 |
| Sarcina lutea | 25 | 12 | 100 | 200 | 400 | do. | do. |
| Staphylococcus aureus | 25 | 12 | 100 | 200 | 400 | do. | do. |
| Streptococcus lactis | 25 | 12 | 100 | 200 | 400 | do. | do. |
| Acaligenes faecalis | 50–100 | >200 | >200 | 200 | 400 | do. | do. |
| Escherichia coli | 50–100 | >200 | do. | >200 | 400 | do. | do. |

Zygosaccharomyces

Table VII-continued

Minimal Inhibitory Concentrations (in ppm.) of
4-Cinnamyl-phenol and Several Alkyl 4-Hydroxybenzoates Against
Bacteria, Yeasts, and Molds

|  | 4-Cinna-myl-phenol | Heptyl-4-hydroxy-benzoate | Amyl 4-hydroxy-benzoate | n-Butyl 4-hydroxy-benzoate | n-Propyl 4-hydroxy-benzoate | Ethyl 4-hydroxy-benzoate | Methyl 4-hydroxy-benzoate |
|---|---|---|---|---|---|---|---|
| *japonicus* | 12 | 12–25 | 50 | 100 | 100–200 | 200 | do. |
| *Candida tropicalis* | 12 | 12–25 | 50 | 100 | 200 | 200 | do. |
| *Pichia chodati* | 25 | >200 | 100 | 100 | 200–400 | >200 | do. |
| *Hansenula anomala* | 50 | >200 | 100 | 100 | 200–400 | do. | do. |
| *Saccharomyces cerevisiae* | 25 | 100 | 50 | 100 | 200 | do. | do. |
| *Torula utilis* | 50 | 25 | 100 | 100 | 200 | do. | do. |
| *Aspergillus flavus* | 100 | >200 | 100 | 200 | 200 | do. | do. |
| *Aspergillus niger* | 50 | do. | 100 | 200 | 200 | do. | do. |
| *Penicillium chrysogenum* | 50 | do. | 100 | 100 | 200 | do. | do. |
| *Rhizopus senti* | 6 | 25 | 50 | 100 | 200 | do. | do. |
| *Botrytis cinerea* | 25–50 | 50–100 | 50 | 100 | 100–200 | 100 | 100 |
| *Byssochlamys fulva* | 25 | >200 | 100 | 100 | 200 | 200 | >200 |
| *Alternaria sp.* | 25 | 50–100 | 50 | 50 | 100–200 | 100 | >200 |

EXAMPLE 3

Two compounds (4-cinnamyl-phenol and 4-cinnamyl-resorcinol) were assayed for effectiveness against bacteria, molds, and yeasts, except that in this case the assays were conducted at different concentrations of each compound and at different pH's in order to determine the minimum concentration of each compound required to inhibit growth at the particular pH.

The results are tabulated below.

EXAMPLE 4

Samples of fruit juice (grape and apple) with and without added 4-cinnamyl-phenol were inoculated with cultures of wild yeast or pure wine yeast (S. cerevisiae) and held at room temperature. The inoculated juices were observed at intervals to detect the time at which fermentation (gas production) began. This is a measure of microbial activity—where the organisms multiply freely, the time for initiation of fermentation is short; conversely, where microbial growth is inhibited the time for initiation of fermentation is long or does not occur at all.

The results are tabulated below.

Table VIII

Effect of pH on Minimal Inhibitory Concentration (ppm.)
of 4-Cinnamyl-phenol and 4-Cinnamyl-resorcinol

|  | 4-Cinnamyl-phenol | | | | | 4-Cinnamyl-resorcinol | | | | |
|---|---|---|---|---|---|---|---|---|---|---|
|  | pH 7 | pH 6 | pH 5 | pH 4 | pH 3 | pH 7 | pH 6 | pH 5 | pH 4 | pH 3 |
| *Bacillus cereus* | 25 | 25 | 25 | 12.5 |  | 200 | 200 | 100 | 6.25 |  |
| *Sarcina lutea* | 25 | 25 | 25 | 12.5 |  | 100 | 100 | 50 | 25 |  |
| *Staphylococcus aureus* | 25 | 25 | 25 | 25 |  | 100 | 100 | 50 | 25 |  |
| *Streptococcus lactis* | 25 | 25 | 25 | 25 |  | 100 | 100 | 50 | 25 |  |
| *Acaligenes faecalis* | 50 | 25 | 25 | 25 |  | 200 | 200 | 100 | 25 |  |
| *Escherichia coli* | 25 | 50 | 50 | 25 |  | 100 | 200 | 100 | 50 |  |
| *Zygosaccharomyces japonicus* |  | 12.5 | 12.5 | 12.5 | 12.5 |  | 100 | 50 | 50 | 50 |
| *Candida tropicalis* |  | 25 | 25 | 25 | 12.5 |  | 75 | 50 | 50 | 50 |
| *Pichia chodati* |  | 50 | 50 | 25 | 12.5 |  | 100 | 150 | 100 | 50 |
| *Hansenula anomala* |  | 50 | 50 | 50 | 25 |  | 100 | 100 | 100 | 75 |
| *Saccharomyces cerevisiae* |  | 25 | 25 | 25 | 12.5 |  | 50 | 50 | 100 | 50 |
| *Geotrichum sp.* |  |  |  |  |  |  |  |  |  |  |
| *Torula utilis* |  | 50 | 50 | 37.5 | 25 |  | 75 | 50 | 75 | 50 |
| *Aspergillus flavus* |  | 100 | 100 | 100 | 50 |  | 200 | 200 | 200 | 100 |
| *Aspergillus niger* |  | 100 | 100 | 75 | 37.5 |  | 200 | 200 | 100 | 100 |
| *Penicillium chrysogenum* |  | 50 | 50 | 50 | 12.5 |  | 100 | 100 | 50 | 50 |
| *Rhizopus senti* |  | 25 | 25 | 25 | 12.5 |  | 100 | 100 | 100 | 50 |
| *Botrytis cinerea* |  | 25 | 25 | 25 | 12.5 |  | 100 | 100 | 75 | 50 |
| *Byssochlamys fulva* |  | 25 | 25 | 25 | 12.5 |  | 100 | 100 | 75 | 50 |
| *Alternaria sp.* |  |  |  | 50 | 12.5 |  |  |  | 75 | 50 |

Table IX

| | | | Amount of | Time for initiation of fermentation, hours | | | | | |
|---|---|---|---|---|---|---|---|---|---|
| Run | Substrate | Inoculum | inoculum, cells/ml. | Zero 4-CP | 12.5 ppm of 4-CP | 25 ppm of 4-CP | 50 ppm of 4-CP | 100 ppm of 4-CP | 200 ppm. of 4-CP |
| 1 | Grape juice | Wild yeast | $10^7$ | 7 | n.d. | 12 | n.d. | 44 | n.d. |
| 2 | do. | do. | $10^3$ | 17 | 17 | 30 | 62 | >96 | n.d. |
| 3 | do. | Wine yeast | $10^5$ | 12 | 22 | 45 | 146 | ∞ | ∞ |
| 4 | do. | do. | $10^2$ | 41 | 75 | ∞ | ∞ | ∞ | ∞ |
| 5 | Apple juice | Wine yeast | $10^5$ | 46 | 42 | 76 | ∞ | ∞ | ∞ |

Influence of 4-Cinnamyl-phenol on Fermentation of Fruit Juice Inoculated with Yeasts Explanation of symbols:
4-CP designates 4-cinnamyl-phenol
n.d. means not determined
∞ means that fermentation did not occur; the organisms had been destroyed.

Having thus described the invention what is claimed is:

1. A composition of matter comprising -
   a. a major proportion of a substance normally subject to microbial spoilage, and
   b. a minor proportion, sufficient to inhibit microbial growth, of 2-methoxy-4-cinnamyl-phenol.

2. A composition of matter comprising -
   a. a major proportion of a substance normally subject to microbial spoilage, and
   b. a minor proportion, sufficient to inhibit microbial growth, of 2-cinnamyl-4-methoxy-phenol.

* * * * *